United States Patent [19]

Bode

[11] 4,174,258
[45] Nov. 13, 1979

[54] SOLID ELECTROLYTE OXYGEN SENSOR WITH ZERO OXYGEN REFERENCE

[75] Inventor: James D. Bode, Royal Oak, Mich.

[73] Assignee: Bendix Autolite Corporation, Fostoria, Ohio

[21] Appl. No.: 902,472

[22] Filed: May 3, 1978

[51] Int. Cl.² ............................................. G01N 27/46
[52] U.S. Cl. ................................. 204/195 S; 204/1 T
[58] Field of Search ............................... 204/15, 195 S

[56] References Cited

U.S. PATENT DOCUMENTS

| | | | |
|---|---|---|---|
| 3,403,090 | 9/1968 | Tajiri et al. | 204/195 S |
| 3,578,578 | 5/1971 | Von Krusenstierna | 204/195 S |
| 3,619,381 | 11/1971 | Fitterer | 204/195 S |
| 4,021,326 | 5/1977 | Pollner et al. | 204/195 S |
| 4,045,300 | 8/1977 | Renet | 204/195 S |
| 4,049,524 | 9/1977 | Togawa et al. | 204/195 S |
| 4,057,477 | 11/1977 | Weyl et al. | 204/195 S |

*Primary Examiner*—T. Tung
*Attorney, Agent, or Firm*—William G. Kratz, Jr.; Raymond J. Eifler

[57] ABSTRACT

A solid electrolyte oxygen gas sensor element 1 comprises an electrolyte body 3 having electrodes 7 and 11 on the outer and inner surfaces 5 and 9 thereof, with the inner surface 9 having a protective means 13 thereon to protect the same from contact with oxygen or oxygen-containing gases so as to provide a substantially zero oxygen reference for the inner surface. The protective means 13 can comprise a coating, or a packing within a tubular electrolyte body, of carbon or a metal which forms an oxide that is stable at the operating temperature of the oxygen sensor element.

16 Claims, 2 Drawing Figures

SOLID ELECTROLYTE OXYGEN SENSOR WITH ZERO OXYGEN REFERENCE

BACKGROUND OF THE INVENTION

The present invention relates to solid electrolyte voltaic oxygen gas sensors such as are operated at high temperatures to measure, for example, the oxygen content of automotive exhaust gases or boiler gases. Such sensors are formed of zirconium dioxide or other oxygen ion transferring composition and are normally stabilized by the addition of oxides of calcium, magnesium, yttrium or the like, as known in the art. Electrodes are formed on both the outside and the inside surfaces of the electrolyte body, generally thimble shaped, such as by applying to the surfaces porous layers of platinum. The outer electrode is exposed to the gas, the oxygen content of which is to be measured, such as automotive exhaust, while the inner electrode is exposed to a reference gas, generally air which contains about 21% oxygen. The air from within the tubular body thus serves as a reference gas establishing a fixed concentration of oxygen, hence a fixed reference voltage on the inner electrode. Any changes that occur in the voltage difference between the inner and outer electrodes therefore reflects a change in the composition of the gas, the oxygen content of which is measured, such as an exhaust gas.

When air is used as a reference, the sensor will give a very low voltage output when the exhaust gas has enough oxygen to exceed the chemical stoichiometric amount needed to react with all the oxidizable materials in the exhaust gas. When the amount of oxygen in the exhaust gas becomes less than the stoichiometric amount required, the voltage of the sensor will suddenly increase approaching 1 v or more as the net amount of oxygen becomes very small. This sudden change in voltage at the stoichiometric oxygen concentration is highly desirable for most applications of this type of sensor. The direction of the voltage change, however, as well as the use of air for the reference do have disadvantages.

One major disadvantage of the sensor voltage increasing when the oxygen concentration of the gas being measured decreases is that it precludes the use of a simple "fail-safe" operation with the sensor. Since a low voltage indicates excess oxygen, control circuits based on such an oxygen sensor automatically call for more fuel, or less air, to balance the combustion process, i.e. they call for a richer combustion mixture. If the oxygen sensor, for some reason, would become inoperative, its voltage output would ordinarily drop to zero or to a very low voltage. Such an output would automatically signal the control circuit to continue enriching the combustion mixture leading to an undesirable increase in air polluting compounds in the exhaust gas. An additional advantage exists when the oxygen sensor is used to help control automotive exhaust mixtures since richer fuel mixtures generally give better automobile driveability and there would be no incentive for the operator to replace a defective sensor.

Another disadvantage of the increase in output voltage of a sensor with a decrease in the oxygen content of the gas being measured is that such a sensor cannot directly replace or be replaced by a resistive-type sensor. A resistive-type oxygen sensor, such as a titanium dioxide oxygen sensor, increases resistance and therefore output voltage in the measuring circuit when the oxygen content increases. The direct interchangeability of voltaic-type oxygen sensor elements of zirconium dioxide with the resistive-type titanium dioxide sensor elements, while a property desired by automotive engineers, is not possible due to the reverse relation between oxygen concentration of the exhaust gas and voltage output evidenced by the two types of sensors.

The use of air as a reference gas in voltaic oxygen sensors has the disadvantage that any small leak or permeability of the sensor electrolyte body leads to a change in the reference side voltage so that it approaches that of the exhaust gas side. Also, if the reference side is deprived of replacement air, such as by blocking of a breathing hole for example, or is supplied with contaminated air, the reference side voltage will change and thus change the sensor output giving an inaccurate reading as to the oxygen content of the gas being measured.

An object of the present invention is to produce a voltaic oxygen sensor element that will overcome the aforementioned disadvantages without basic changes in the overall sensor design. In the present invention, a coating is applied to the inner surface of the solid electrolyte body, the coating being formed of a material which forms an oxide which is stable at operating temperatures of the sensor element, so as to protect the inner surface from contact with oxygen-containing gases within the tubular body, thus replacing the commonly used air reference with a very low, essentially zero, oxygen concentration reference. The reference side of the solid electrolyte body is thus covered with a material, stable at the operating temperatures of the sensor, that will react with, bind or remove from contact with the reference side of the electrolyte body, any oxygen present or appearing on the reference side.

With an effective zero oxygen concentration reference, the voltaic-type zirconium oxygen sensor would show a direct rather than a reverse voltage output relation to the oxygen concentration in the exhaust gas. When less than the stoichiometric amount of oxygen was present in the gas on both sides of the electrolyte body, the electrolyte would see very low concentrations of oxygen so this difference in voltage, the sensor output, would be small. When the oxygen content of the exhaust gas exceeded the stoichiometric amount the voltage would suddenly increase and would again approach 1 v or more as the oxygen content increased. The "zero" oxygen reference sensor would, in effect, operate as the mirror image of the present air reference sensor. Consequently, a low voltage output would indicate a low oxygen content in the exhaust gas and call for more air, or less fuel, in the combustion mixture. This would give a direct fail-safe feature to the sensor. In addition, with this relationship between voltage output and the oxygen content of the exhaust gas, these voltaic sensor elements would be interchangeable with resistive-type sensor elements.

BRIEF SUMMARY OF THE INVENTION

A solid electrolyte oxygen gas sensor 1 having a substantially zero oxygen reference comprises a solid electrolyte body 3 for transferring oxygen ions having an outer surface 5 with a conductive catalyst electrode 7 thereon for contact with a gas, the oxygen content of which is to be measured, and an inner surface 9 with a conductive electrode 11 thereon, with protective means 13 on the inner surface for protecting the inner surface from contact with oxygen-containing gases, the protective means 13 preferably comprising a coating or packing of carbon or a metal that forms an oxide that is stable at the operating temperatures of the sensor element.

DESCRIPTION OF THE PREFERRED EMBODIMENT

Figure 1:
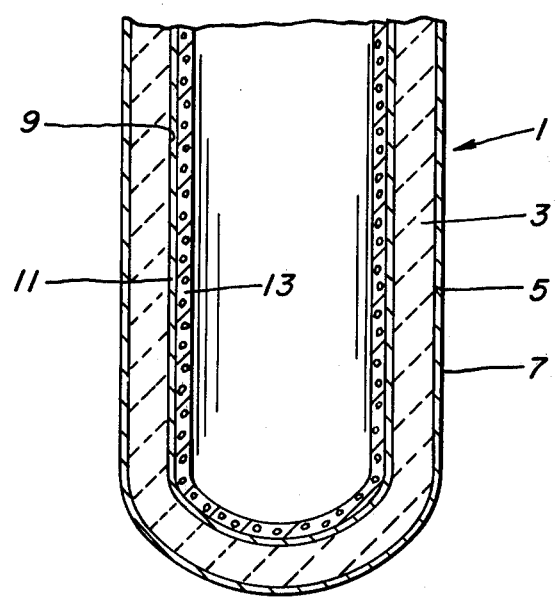
FIG. 1 is a schematic cross-sectional view of an embodiment of a solid electrolyte sensor element of the present invention.

Referring now to FIG. 1, there is illustrated one embodiment of an oxygen sensor element 1 which is prepared according to the present invention. As illustrated, the sensor element 1 comprises a solid electrolyte tubular body 3 for transferring oxygen ions, this body generally is shaped into a hollow tubular or thimble-like structure. The electrolyte body 3 is composed of known oxygen-ion transferring materials such as zirconium dioxide, which may contain various stabilizing materials such as calcium oxide, yttrium oxide, thorium dioxide, or the like, the body being open at one end and closed at the other end.

On the outer surface 5 of the electrolyte body 3 there is applied a conductive catalyst electrode 7, which electrode is for contact with a gas, the oxygen content of which is to be determined. As is known, this conductive catalyst electrode 7 may completely cover the outer surface 5 of the electrolyte body 3, or the electrode may cover only a sufficient area to provide a conductive path along said outer surface. The conductive catalyst electrode is usually formed of platinum or a platinum family catalyst and may, if desired, have a protective porous coating (not shown) thereover to protect the same from attrition or wear during operation at elevated temperatures.

On the inner surface 9 of the electrolyte body 3 there is provided a conductive means 11 which may be a strip of conductive material or a film or layer of conductive material which is applied as an electrode in a known manner. This conductive electrode may also be formed of a catalytic material such as platinum or a platinum family metal catalyst in which structures the inner conductive electrode means will also evidence catalytic activity.

In conventional sensor elements the inner surface 9 of the electrolyte and the conductive electrode 11 thereon are exposed to air as a reference gas. In the present invention, however, the inner surface 9 is protected from any contact with air or other oxygen-containing gas from within the electrolyte tubular body by a protective means on the inner surface for protecting that surface and providing a substantially zero oxygen reference for that surface.

As illustrated in FIG. 1, a coating 13 of material is applied over the inner surface for the electrolyte body to protect that surface from contact with air or other oxygen-containing gases. The coating 13 extends completely over the inner surface so that the surface is completely shielded from any air or oxygen-containing gases from within the tubular body. The material used as the protective coating is one which will readily react with and retain oxygen at the operating temperature of the sensor element so as to provide a very low, essentially zero, concentration of oxygen at the inner surface of the solid electrolyte body.

Figure 2:
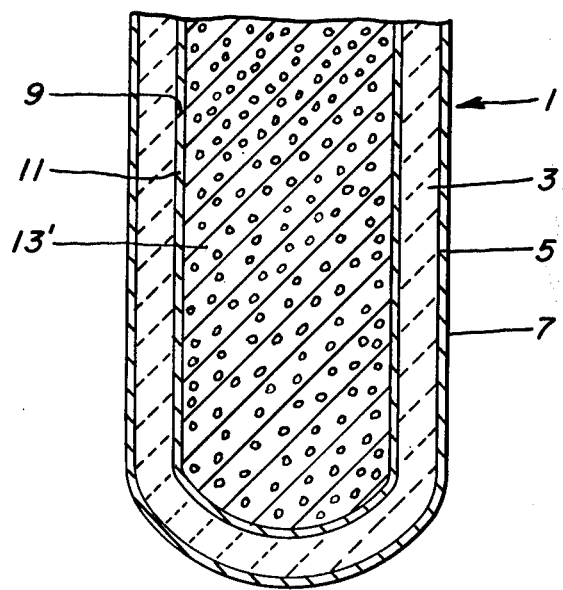
FIG. 2 is a schematic cross-sectional view of another embodiment of a solid electrolyte sensor element of the present invention.

Materials that are preferred for use as a protective means on the inner surface of the electrolyte body are carbon or metals that form oxides that are stable at the operating temperature of the sensor element. The carbon may be in the form of activated charcoal, colloidal graphite or lamp black or other carbonaceous material. The metals which may be used as a protective means are those which form oxides that are thermally stable at temperatures of about 800° C.–1200° C., which temperatures correspond to the higher operating temperatures of oxygen sensors used in automotive exhaust systems. In automotive exhaust systems, oxygen sensors generally operate from 350° to 850° C., reaching the higher temperatures only under conditions of heavy loads and high accelerations. Such metals includes aluminum, calcium, magnesium, titanium, zirconium, yttrium, tantalum and the like.

Where carbon is used as the protective material, the availability of different forms of carbon make it a convenient and inexpensive material that can serve different functions. For example, a graphite coating on the inner surface of the electrolyte body could serve as both an electrode means and a protective means. Activated charcoal or colloidal graphite could serve to assure protection by removal of oxygen at comparatively low temperatures where reaction between carbon and oxygen is ordinarily slow. In the embodiment illustrated in FIG. 2, wherein the protective means comprises a packing 13' within the tubular body 3, an activated charcoal material could also serve as a sink for the carbon monoxide and dioxide formed when carbon reacts with oxygen forming a completely sealed reference side, if desired. In addition, a catalytic material such as platinum or palladium could be dispersed in the carbon to aid in and assure removal at low temperatures.

The formation of the coating on the inner surface of the solid electrolyte body may be achieved by known coating processes such as by brushing or spraying or by decomposing compositions containing the required materials by pyrolysis or the like.

The sensor elements of the present invention provide for use of a zero oxygen reference system where air or other oxygen-containing gases are kept from contact with the inner surface. These elements are voltaic-type sensors that are interchangeable with resistive-type sensors in measuring systems for automotive exhaust analysis, since with the substantially zero oxygen reference, the voltage output will increase with an increase in the oxygen content of the exhaust gas.

I claim:

1. An oxygen gas sensor element comprising a solid electrolyte body for transferring oxygen ions, the body having an outer surface having a conductive catalyst electrode thereon for contact with a gas, the oxygen content of which is to be measured, and an inner surface having a conductive electrode thereon, the improvement comprising:

protective means over the conductive electrode and the inner surface of the solid electrolyte body for protecting said inner surface from contact with oxygen-containing gases and providing a substantially zero oxygen reference for said inner surface.

2. In an oxygen gas sensor element as defined in claim 1, the improvement wherein said means over the conductive electrode and the inner surface comprise a coating thereon, said coating comprising a protective material which forms an oxide which is stable at the operating temperature of the sensor element.

3. In an oxygen gas sensor element as defined in claim 1, the improvement wherein said means over the conductive electrode and the inner surface comprise a coating of a protective material selected from the group consisting of carbon and a metal which forms an oxide stable at the operating temperature of the sensor element.

4. In an oxygen gas sensor element as defined in claim 1, the improvement wherein said solid electrolyte body is a tubular body and wherein said means over the conductive electrode and the inner surface comprise a packing within the tubular body and covering said inner surface, the packing comprising a protective material selected from the group consisting of carbon and a metal which forms an oxide stable at the operating temperature of the sensor element.

5. In an oxygen gas sensor element as defined in claim 3 or 4, the improvement wherein said protective material comprises carbon.

6. In an oxygen gas sensor element as defined in claim 3 or 4, the improvement wherein said protective material comprises a metal selected from the group consisting of aluminum, calcium, magnesium, tantalum, titanium, zirconium and yttrium.

7. In an oxygen gas sensor element as defined in claim 3 or 4, the improvement wherein the conductive electrode on said inner surface is a conductive catalytic electrode.

8. In an oxygen gas sensor element as defined in claim 3 or 4, the improvement wherein a catalytic material is dispersed in said protective material.

9. In an automotive oxygen gas sensor element, for use in determining the oxygen content of an automotive exhaust gas, said element comprising a solid electrolyte tubular shaped hollow body of stabilized zirconium dioxide and wherein the outer surface of the tubular body has a conductive catalyst electrode thereon and the inner surface of the tubular body has a conductive electrode thereon, the improvement comprising:

protective means over the conductive electrode and the inner surface of the tubular body for protecting said inner surface from contact with oxygen-containing gases from within said hollow tubular body and providing a substantially zero oxygen reference for said inner surface.

10. In an automotive gas sensor element as defined in claim 9, the improvement wherein said protective means comprise a protective material selected from the group consisting of carbon and a metal which forms an oxide stable at the operating temperature of the automotive oxygen gas sensor element.

11. In an automotive oxygen gas sensor element as defined in claim 10, the improvement wherein said protective means comprise said protective material formed as a coating on said inner surface.

12. In an automotive oxygen gas sensor as defined in claim 10, the improvement wherein said protective means comprise said protective material formed as a packing within said hollow tubular body.

13. In an automotive oxygen gas sensor as defined in claim 11 or 12, the improvement wherein said protective material comprises carbon.

14. In an automotive oxygen gas sensor as defined in claim 11 or 12, the improvement wherein said protective material comprises a metal selected from the group consisting of aluminum, calcium, magnesium, tantalum, titanium, zirconium and yttrium.

15. In an automotive oxygen gas sensor as defined in claim 11 or 12, the improvement wherein the conductive electrode on said inner surface is a conductive catalytic electrode.

16. In an automotive oxygen gas sensor element as defined in claim 11 or 12, the improvement wherein a catalytic material is dispersed in said protective material.

* * * * *